United States Patent [19]

Shtull

[11] Patent Number: 4,790,041
[45] Date of Patent: Dec. 13, 1988

[54] PILLOW FOR RITUAL CIRCUMCISIONS AND METHOD

[76] Inventor: Kiva Y. Shtull, 4130 Ellison Rd., South Euclid, Ohio 44121

[21] Appl. No.: 117,057

[22] Filed: Nov. 5, 1987

[51] Int. Cl.$^4$ ............................................. A47C 27/15
[52] U.S. Cl. ........................................... 5/431; 5/424; 108/43; 269/328
[58] Field of Search ................ 5/434, 431, 448, 481, 5/436, 443, 425, 424; 269/328; 128/133, 134; 108/43

[56]  References Cited

U.S. PATENT DOCUMENTS

| | | | |
|---|---|---|---|
| 3,148,384 | 9/1964 | Sarnie et al. | 5/431 |
| 3,545,016 | 12/1970 | Schorken | 4/472 |
| 4,235,472 | 11/1980 | Sparks et al. | 5/434 |
| 4,441,221 | 4/1984 | Enste et al. | 5/431 |
| 4,494,261 | 1/1985 | Morrow | 5/434 |
| 4,566,449 | 1/1986 | Smith | 128/133 |
| 4,584,730 | 4/1986 | Rajan | 5/431 |
| 4,631,766 | 12/1986 | Semmler et al. | 5/431 |

FOREIGN PATENT DOCUMENTS 641616  12/1963  Belgium ................................. 5/436

*Primary Examiner*—Alexander Grosz
*Attorney, Agent, or Firm*—Renner, Otto, Boisselle & Sklar

[57] ABSTRACT

A pillow (1) for ritual circumcisions, includes a main support body (4), bottom walls (6) proximate a pair of opposite edges of the bottom of the main support body for defining therewith a contoured area (12) to fit relatively securely on the lap of a person, and top walls (5) proximate a pair of opposite edges of the top of the main support body for defining therewith a contoured area (11) to receive and to support a baby therein.

A method of performing ritual circumcision during which a baby is held on the lap of a person by using a pillow having a predetermined bottom concave contour having an axis and a predetermined concave contour having an axis, includes placing a pillow on the lap of such person, generally centering and stabilizing such the pillow on the lap of such person according to such contour, and placing the baby on the top of such pillow generally centered relative to the concave contour thereof and extending along the axis of such contour.

13 Claims, 1 Drawing Sheet

PILLOW FOR RITUAL CIRCUMCISIONS AND METHOD

TECHNICAL FIELD

This invention relates generally, as indicated, to pillows, and, more particularly, to pillows for use during ritual circumcision procedures.

BACKGROUND

According to Jewish tradition a male baby usually would be circumcised on the eighth day following birth. The ritual circumcision typically is carried out by the surgeon or "mohel" while the baby is held on the lap of an honoree, i.e., another person to whom the honor of holding the baby is given. For convenience and comfort a bed pillow usually is placed on the honoree's lap and the baby is placed on the pillow.

As is well known by those experienced as such honoree's and by others who have participated in and observed such ritual circumcisions, it is evident that there is some feeling of insecurity holding the baby. The baby is tiny and the honoree may be uncomfortable trying to take care to hold the baby securely while minimizing discomfort to the baby.

A difficulty that the surgeon or "mohel" may encounter is the difference in circumstances in each circumcision. Specifically, if the person holding the baby is very insecure, the baby may wiggle too much, making the surgery more difficult. Also, the pillows on which the babies are held during circumcision vary from home to home, e.g. in softness, plushness, fullness, etc., and, therefore, the babies would be positioned in different ways.

BRIEF SUMMARY OF THE INVENTION

According to the present invention, there is provided a pillow specifically designed to facilitate ritual circumcisions. Such pillow is placed on the legs/knees of the honoree and provides comfort and security for the baby, accurate comfortable positioning for the surgeon "mohel", and confidence for the honoree. The pillow eliminates the need to restrain the baby in an unnatural and uncomfortable position during the ritual circumcision.

Briefly, according to the present invention, then, a pillow for ritual circumcisions includes a main support body, bottom walls proximate a pair of opposite edges of the bottom of the main support body for defining therewith a contoured area to fit relatively securely on the lap of a person, and top walls proximate a pair of opposite edges of the top of the main support body for defining therewith a contoured area to receive and to support a baby therein.

According to the method of the invention, a ritual circumcision is performed during which a baby is held on the lap of a person by using a pillow having a predetermined bottom concave contour having an axis and a predetermined concave contour having an axis, and includes the steps of placing a pillow on the lap of such person, generally centering and stabilizing such pillow on the lap of such person according to such contour, and placing the baby on the top of such pillow generally centered relative to the concave contour thereof and extending along the axis of such contour.

To the accomplishment of the foregoing and related ends, the invention, then, comprises the features hereinafter fully described and particularly pointed out in the claims, the following description and the annexed drawings setting forth in detail an illustrative embodiment of the invention, this being indicative, however, of but one of the various ways in which the principles of the invention may be employed.

It will be appreciated that the claims are intended to cover not only the particular means, elements and inventions set forth therein, but also equivalent means, elements and inventions.

BRIEF DESCRIPTION OF THE DRAWINGS

In the annexed drawings.

DESCRIPTION OF THE PREFERRED EMBODIMENT

Figure 1:
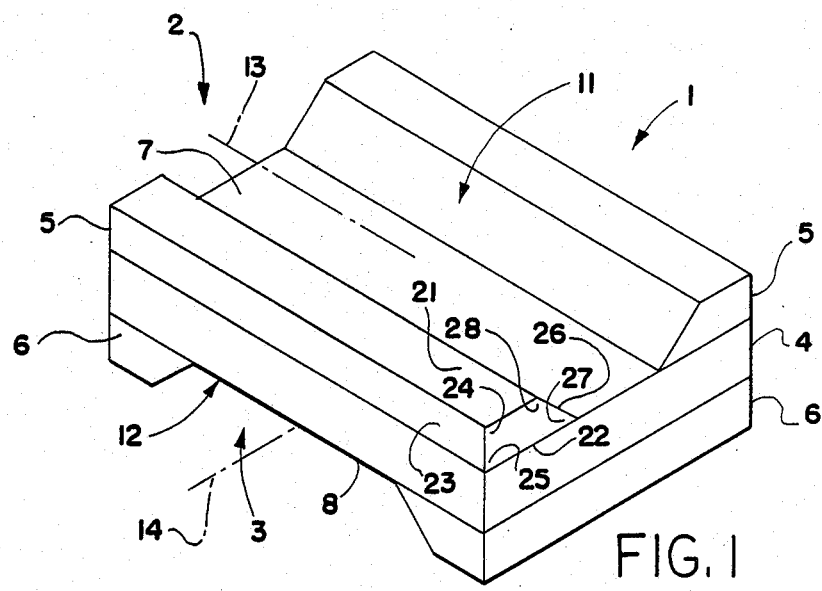
FIG. 1 is an isometric view of a pillow according to the preferred embodiment and best mode of the present invention.
Figure 4:
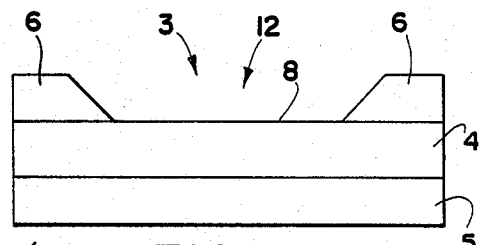
FIG. 4 is a side view of the pillow looking generally in the direction of the arrows 4—4 of FIG. 2.
Figure 3:
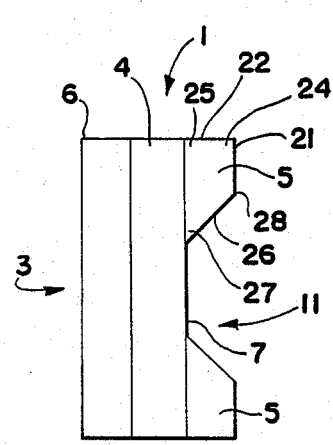
FIG. 3 is an end view of the pillow looking generally in the direction of the arrows 3—3 of FIG. 2.
Figure 2:
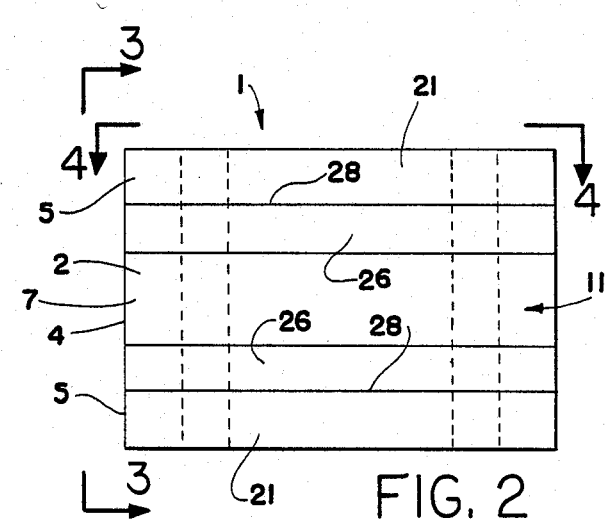
FIG. 2 is a top plan view of the pillow of FIG. 1.

Referring, now, in detail to the drawings, wherein like reference numerals designate like parts in the several figures, a pillow according to the invention is shown at 1 in FIGS. 1-4.

The pillow 1 has a top 2 and a bottom 3. The pillow 1 is formed of a main support body 4 having a pair of top walls 5 and a pair of bottom walls 6. Respective pairs of walls 5, 6 cooperate with the respective top 7 and bottom 8 surfaces of the main support body 4 to define respective top and bottom contoured U-shape or V-shape concave areas 11, 12.

Each such contoured area 11, 12 has a generally axial extent represented by axis lines 13, 14. In the preferred embodiment those axes are orthogonal, as is illustrated, so that the baby would like cross-wise relative to the directional extent of the legs of the holder. However, if desired, the axes may be parallel.

The several portions of the pillow 1 preferably are made of high density polyurethane foam #1835. Such material typically weighs about 1.8 pounds per cubic foot and requires about 35 pounds per square inch to compress the foam material to one half thickness. Other materials also may be used for the pillow 1. Preferably, though, such materials should have a reasonable degree of rigidity to hold shape and of resiliency to fit relatively securely to the lap of a person and to support in comfort a baby placed thereon especially without concentrated force at pressure points where the baby is in direct contact with the pillow. Furthermore, preferably the material of which the pillow is made should not have a "cold" feel, such as metal; rather, it should have a "warm" feel, as foam does, in order to maximize temperature comfort of the baby.

Also, although not shown, the pillow may be covered with a fabric for aesthetics, for protection of the foam material, and/or to provide a surface that can be readily washed or otherwise cleaned for general cleanliness purposes desired in the area of surgical procedure. The latter especially is achieved if the fabric cover were removable for cleaning between each use. Moreover, if desired, the pillow may be of a type that is not used repeatedly; rather, it may be provided as a cherished memento to the occasion.

According to the preferred embodiment and best mode of the invention, the main support body 4 is a flat rectangular sheet of foam. Exemplary size dimensions would be about twenty-three inches long by about sixteen inches wide by about three inches thick. Other size dimensions also may be used, depending on circumstances, e.g., larger sizes may be used for larger people holding the pillow and/or for larger than average babies. However, it has been found that the width dimension is adequate to fit comfortably and securely on the lap of a person; and the length dimension is adequate to hold and securely and comfortably to support relatively long babies. The preferred thickness dimension has been found to be satisfactory to place the baby at a good height for the surgery, although thicker or thinner materials may be preferred and specifically tailored to the comfort and convenience of the surgeon or "mohel". Too high a pillow (or too thick a main support body) usually would not be preferred, though, because of the possible instability of the pillow while it is resting on the lap of the person holding the same.

The just-above-mentioned length and width dimensions for the main support body are particularly advantageous, as described, when the axes 13, 14 are orthogonal. However, in the event that it is desired that the axes be parallel, preferably the width dimension would be made longer, e.g. also to about twenty-three inches, in order to provide adequate length to hold and securely and comfortably to support relative long babies.

Preferably (for convenience and cost efficiency) the top walls 5 and the bottom walls 6 are formed of the same material and are of the same shape, although the lengths thereof may be different in order to correspond to the length or width dimension of the main support body 4 to which they are fastened. The top and bottom walls preferably are formed of the same type of foam material of which the main support body 4 is formed. The top and bottom walls 5, 6 are attached to the main support body 4 proximate respective pairs of edges thereof, as can be seen in the drawings.

The top and bottom walls 5, 6 may be attached to the main support body 4 by glue or other adhesive material; an example is a glue material sold under the trademark K-GRIP, which is an air spray glue. Other materials also may be used to attach the top and bottom walls 5, 6 to the main support body 4. Further, as an alternative embodiment, which is not illustrated in the drawings, the pillow 1 may be formed by molding the same in a mold using conventional molding techniques so that the entire pillow is formed of a single integral material.

The top and bottom walls 5, 6 preferably are elongate strips of foam that have a trapezoidal cross-section, as is seen in the drawings. Two of the surfaces 21, 22 of such a rectangle meet a third surface 23 at respective right angles 24, 25. The surfaces 21, 22 also meet a fourth surface 26 to complete the trapezoidal cross-section at respective acute and obtuse angles 27, 28. By mounting the top and bottom walls 5, 6 to respective top and bottom surfaces 7, 8 of the main support body 4 in the illustrated manner, the fourth surface 26 provides a slope from the plane of the surface 21 toward the a center portion of a respective surface of the main support body. Thus, the top and bottom walls 5, 6 in effect cooperate with the main support body 4 to define contoured concave areas 11, 12 of upright and inverted U- or V-shape, as is clearly seen in the drawings in a sense to provide a lead-in function to locate the baby generally in the center along the axis 13 and to locate the legs/knees of the holder centered relative to the axis 14.

In using the pillow 1 of the present invention the pillow the contoured bottom or underside 3 is placed on the lap of a person who typically would be seated on a chair. The baby then is placed on the contoured top 2 to be cradled in a position that is relatively natural, namely with the hips flexed and abducted away from the midline of the body. The contoured bottom 3 helps locate the pillow 1 with respect to the lap of the holder; and gives the holder a sense of comfort and security, i.e., secure or confident that neither the pillow nor the baby will not easily fall. The pillow 1 also can be so placed that the end thereof close to the torso of the holder can be drawn into engagement with the torso in order to enhance such secure holding in place on the lap of the person.

Still further, due to the fact that the baby would be held, most preferably, transverse to the direction of extension of the legs of the holder and to the fact that the baby may be placed slightly closer to one of the top walls than the other, while still being in a comfortable and easily accessed position for the surgery, it would be tolerable for the top surface 7 of the main support body to slope slightly down and away from the torso of the holder without impeding the surgery. Therefore, in case the legs of the holder are not long enough to hold the top surface of the main support body 4 in a perfectly horizontal position, the surgery would not be impeded; accordingly, the holder would not have to undergo the further discomfort of having to stretch his/her legs to hold the baby in a horizontal position. Rather, that generally horizontal orienting of the baby can be achieved by relying on the cooperative relation of the slope of the lower top wall and the adjacent top surface of the main support body 4.

Summarizing the method of the present invention, i.e. to perform ritual circumcision during which a baby is held on the lap of a person by using a pillow having a predetermined bottom concave contour 12 having an axis and a predetermined concave contour having an axis, the pillow is placed on the lap of such person. The pillow bottom walls 6 and bottom 8 of the main support body 4, provide a tapered lead in toward the center thereof generally to center and to stabilize such the pillow on the lap of such person according to such contour. The baby is placed on the top 2 of such pillow 1 generally centered relative to and according to the tapered or concave contour 11 thereof and extending along the axis of such contour. Finally, the legs of the baby can be conveniently held in place against the soft foam of the pillow to provide clear, convenient, and safe access for performing the circumcision surgery.

STATEMENT OF APPLICATION

It will be appreciated that the present invention may be used to facilitate ritual circumcisions and to enhance the safety thereof due to the ability to hold the baby securely and comfortably and due to the comfort and confidence supplied the holder.

I claim:

1. A pillow for ritual circumcisions, comprising a main support body having a substantially continuous top and a substantially continuous bottom, bottom wall means proximate a pair of opposite edges of the bottom of said main support body for defining therewith a contoured area to fit relatively securely on the lap of a person, and top wall means proximate a pair of opposite edges of the top of said main support body for defining therewith a contoured area to receive and to support a baby therein, and wherein said top wall means and the top of said main support body have an overall length long enough to hold a baby from head to toe, said bottom wall means include elongate strips having a sloping surface to provide a contour with the bottom of said main support body to cooperate with the lap portion of a person to facilitate relatively secure positioning on the lap over the legs of such person, and said bottom wall means and the bottom of said main support body have inverted U-shape cross-section with an axis in one direction, and said top wall means and the top of said main support body have U-shape cross-section.

2. The pillow for ritual circumcisions according to claim 1, wherein said main support body comprises foam material.

3. The pillow for ritual circumcisions according to claim 1, wherein said main support body is relatively solid to provide warmth for a baby placed thereon.

4. The pillow for ritual circumcisions according to claim 1, wherein said main support body is resilient to retain a baby in comfort thereon.

5. The pillow for ritual circumcisions according to claim 1, wherein said bottom wall means are tapered to guide the legs of a person to correct position relative to the pillow.

6. The pillow for ritual circumcisions according to claim 1, wherein said main support body and bottom wall means are foam and are glued together.

7. The pillow for ritual circumcisions according to claim 1, wherein said top wall means are cooperatively contoured with the top of said main support body to cradle a baby in natural position.

8. The pillow for ritual circumcisions according to claim 1, wherein said top wall means are tapered to provide a sloped lead in to center the baby relative to the top of the pillow and to hold in place without pressure points.

9. A pillow for ritual circumcisions, comprising a main support body having a substantially continuous top and a substantially continuous bottom, bottom wall means proximate a pair of opposite edges of the bottom of said main support body for defining therewith a contoured area to fit relatively securely on the lap of a person, and top wall means proximate a pair of opposite edges of the top of said main support body for defining therewith a contoured area to receive and to support a baby therein, wherein said top wall means and the top of said main support body have an overall length long enough to hold a baby from head to toe, and said bottom wall means include elongate strips having a sloping surface to provide a contour with the bottom of said main support body to cooperate with the lap portion of a person to facilitate relatively secure positioning on the lap over the legs of such person, and wherein said bottom wall means and the bottom of said main support body have inverted U-shape cross-section with an axis in one direction, and said top wall means and the top of said main support body have U-shape cross-section with an axis generally perpendicular to the first-mentioned axis.

10. The pillow for ritual circumcisions according to claim 9, wherein said main support body and said top wall means are foam and are glued together.

11. The pillow for ritual circumcisions according to claim 9, wherein said top wall means are elongate strips having a sloping surface to provide contour to center a baby therebetween.

12. The pillow for ritual circumcisions according to claim 9, wherein said bottom wall means and said top wall means have the same cross-section and are of the same material but of different length.

13. The pillow for ritual circumcisions according to claim 12, wherein in plan view the pillow has a rectangular shape with width and length dimensions, and wherein the width of the pillow is of a size to span the lap of a person and is relatively shorter than the length, and wherein the length is of a size to hold the length of a baby during a circumcision procedure.

* * * * *